United States Patent [19]

Levin

[11] Patent Number: 5,637,750
[45] Date of Patent: Jun. 10, 1997

[54] METHOD FOR THE PREPARATION OF 2 HYDROXYBENZONITRILE

[75] Inventor: Daniel Levin, Manchester, United Kingdom

[73] Assignee: Zeneca Limited, London, England

[21] Appl. No.: 507,241

[22] PCT Filed: Feb. 11, 1994

[86] PCT No.: PCT/GB94/00277

§ 371 Date: Aug. 18, 1995

§ 102(e) Date: Aug. 18, 1995

[87] PCT Pub. No.: WO94/19317

PCT Pub. Date: Sep. 1, 1994

[30] Foreign Application Priority Data

Feb. 19, 1993 [GB] United Kingdom ............... 9303334

[51] Int. Cl.$^6$ .................... C07C 253/14; C07C 253/16
[52] U.S. Cl. ................................. 558/314; 558/315
[58] Field of Search ............................. 558/315, 312, 558/314

[56] References Cited

U.S. PATENT DOCUMENTS 4,133,834  1/1979  Pickens ..................... 260/566 A

FOREIGN PATENT DOCUMENTS 80700    6/1983  European Pat. Off. .
1447114  8/1976  United Kingdom .

OTHER PUBLICATIONS

Van Es: "A Convenient one-step conversion of aldehydes into nitriles", Journal of the Chemical Society, 1965, p. 1564.

Ganboa, et al: "Reagents and synthetic methods 23. Easily one-flask conversion of aromatic aldehyde to nitriles", Synthetic Communications, vol. 13, No. 3, 1983, pp. 219–224.

Casiraghi, et al: "Selective Reactions using Metal Phenoxides. Part 1. Reactions with Formaldehyde", Journal of the Chemical Society, 1978, pp. 318–321.

*Primary Examiner*—Johann Richter
*Assistant Examiner*—Ebemezer Sackey
*Attorney, Agent, or Firm*—Cushman Darby & Cushman IP Group Pillsbury Madison & Sutro, L.L.P.

[57] ABSTRACT

A method for the preparation of a 2-hydroxybenzonitrile which comprises reacting hydroxylamine with a 2-hydroxyarylaldehyde which is at least partially in the form of a salt and/or complex of a metal of Group II, Group III, Group IVA or Group VIA of the Periodic Table and dehydrating the 2-hydroxyarylaldoxime so formed.

18 Claims, No Drawings

METHOD FOR THE PREPARATION OF 2 HYDROXYBENZONITRILE

This application is a 371 of PCT/GB94/00277 filed Feb. 11, 1994.

This invention relates to a chemical process and more particularly to a method for the preparation of ortho-hydroxy substituted aromatic nitriles.

The preparation of aromatic nitriles by subjecting the corresponding aldoximes to the action of dehydrating agents is a well documented reaction, a number of suitable dehydrating agents having been described in the prior art. The aldoximes themselves may be obtained in conventional manner by reacting the corresponding aromatic aldehydes with hydroxylamine. In practice, the hydroxylamine is usually employed in the form of a salt, for example hydroxylammonium sulphate or chloride, and the reaction is performed in the presence of an acid-binding agent such as sodium carbonate which reacts with the liberated acid forming sodium sulphate or chloride, which has to be disposed of, and carbon dioxide. Since the reaction is commonly carried out in a two-phase aqueous and organic solvent medium, the evolution of carbon dioxide can cause loss of organic solvent with economic and environmental consequences unless appropriate and often expensive precautions are taken.

It is also known to prepare nitriles directly from the corresponding aldehydes. Since hydroxylamine or a material capable of generating hydroxylamine in situ is generally employed as one of the reactants, the reaction is assumed to proceed via the intermediacy of aldoximes but their isolation can be avoided. Thus, Ganboa and Paloma (Synthetic Communications, 13(3), 219–224, 1983) have described the preparation of aromatic nitriles by a one-pot method from aldehydes, hydroxylamine hydrochloride, magnesium sulphate (presumably functioning as dehydrating agent) and p-toluenesulphonic acid as catalyst. The same authors (Synthetic Communications, 13(12), 999–1006, 1983) have also described a one-pot method for preparing aromatic nitriles from aldehydes, hydroxylamine hydrochloride or nitromethane in acetic acid media using polyphosphoric acid as dehydrating agent.

The aromatic nitriles prepared by the dehydration of aldoximes or directly from aldehydes have included 2-hydroxybenzonitrile, a chemical intermediate useful in the production of agricultural chemicals. The preparation of this compound by heating salicylaldoxime in acetic anhydride has been described by Victor Meyer (Chem. Ber., 26, 1254, 1893) and the preparation of the same compound by refluxing a solution of salicylaldehyde in formic acid with hydroxylamine hydrochloride and sodium formate has been reported by van Es (J. Chem. Soc., 1965, 1564).

It has now been found that ortho-hydroxy substituted aromatic nitriles (hereinafter referred to as 2-hydroxybenzonitriles) can be smoothly and economically prepared from 2-hydroxyarylaldehydes if the latter are used, at least partially, in the form of a salt and/or complex of certain metals as hereinafter described. In some cases, a much faster oximation reaction occurs than is the case in the conventional processes and, furthermore, integration of the oximation reaction with a formylation for preparing the aldehyde allows additional operational savings.

Accordingly, the present invention provides a method for the preparation of a 2-hydroxybenzonitrile which comprises reacting hydroxylamine with a 2-hydroxyarylaldehyde which is at least partially in the form of a salt and/or complex of a metal of Group II, Group III, Group IVA or Group VIA of the Periodic Table and dehydrating the 2-hydroxyarylaldoxime so formed.

The Periodic Table referred to herein is the one designated as the "previous IUPAC form" on the front inside cover of the 74th edition of the "Handbook of Chemistry and Physics" published by CRC Press.

As examples of 2-hydroxyarylaldehydes which may be used in the method of the invention, there may be mentioned salicylaldehyde and ring-substituted salicylaldehydes wherein the aromatic ring may carry from one to four substituents in addition to the hydroxy and formyl groups. Examples of suitable substituents include halogen atoms and alkyl, cycloalkyl, aralkyl, aryl, alkaryl, alkoxy, aryloxy, acyl or hydroxy groups.

In accordance with the invention, the 2-hydroxyarylaldehyde is employed, at least partially, in the form of a salt, that is to say an aryloxide, and/or a complex of a metal of Group II, Group III, Group IVA or Group VIA of the Periodic Table. As examples of particularly suitable metals, there may be mentioned magnesium (Group IIA), aluminium (Group IIIB), titanium and zirconium (Group IVA) and chromium (Group VIA). The metal salt or complex may be pre-formed or may be generated in the reaction mixture, perhaps only transiently and possibly in equilibrium with one or more other derivatives of the metal.

Reaction conditions suitable for the preparation of 2-hydroxyarylaldehydes in the form of magnesium salts have been described in our EP-A-0529870.

Conditions under which 2-hydroxyarylaldehydes may be prepared in the presence of compounds of aluminium, titanium, zirconium and chromium have been described in EP-A-0077279, EP-A-0106653 and U.S. Pat. No. 4,231,967 and these conditions may be expected to lead to the formation of the 2-hydroxyarylaldehyde, at least partially, in the form of salts and/or complexes of said metals. Titanium compounds which may be used in the preparation of the 2-hydroxyarylaldehyde include titanium (IV) derivatives. Suitable titanium (IV) derivatives include compounds of the formula

(1)

wherein each of W, X, Y and Z, independently, represents a halogen atom or an alkoxy, aryloxy, alkaryloxy, aralkoxy, acyloxy or cyclopentadienyl group or a residue of a β-diketone, a hydroxyquinoline or an optionally substituted 2-hydroxybenzaldehyde, or two of W, X, Y and Z together represent an oxygen atom, each of the remaining two, independently, representing a halogen atom or an alkoxy, aryloxy, aralkoxy, alkaryloxy or acyloxy group or a residue of a β-diketone, a hydroxyquinoline or an optionally substituted 2-hydroxybenzaldehyde. Generally, the alkyl or acyl part of a group W, X, Y or Z will contain up to 22 carbon atoms and the aryl part will be phenyl. Specific examples of titanium (IV) derivatives include titanium tetraisopropoxide, titanium tetrabutoxide and titanium tetraphenoxide.

In performing the method of the invention, the hydroxylamine may advantageously be used in the form of a salt, for example an aqueous solution of a salt. Suitable salts include hydroxylammonium bromide, phosphate, nitrate and acetate but especially the sulphate.

When the hydroxylamine is employed in the form of a salt and the hydroxyarylaldehyde is used in partial salt form, the metal being present in less than a chemically equivalent amount relative to the hydroxyarylaldehyde, for example a catalytic amount of titanium, it will usually be necessary to perform the oximation reaction in the presence of a base.

Suitable bases include alkali metal hydroxides, carbonates, acetates and the like and nitrogenous bases. When the metal, for example magnesium, is used in at least a chemically equivalent amount relative to the hydroxyarylaldehyde, the addition of a further base as acid-binding agent is not usually necessary.

The oximation reaction may be conveniently performed in a suitable solvent medium at temperatures of from 30° to 150° C. although somewhat lower or higher temperatures may be employed if desired. Suitable solvent media include organic solvents such as alcohols in which both the hydroxyarylaldehyde and the hydroxylamine are soluble to a significant extent. It is preferred, however, to employ the hydroxylamine or salt thereof in the form of an aqueous solution. The hydroxyaldehyde, being at least partially in the form of a salt and/or complex of the metal, may, depending upon its structure and also upon the degree of ionisation, be used as such or in the form of a solution or dispersion in water or in a water-miscible or water-immiscible organic solvent. Preferred solvent systems include mixtures of water and an aromatic hydrocarbon such as toluene or xylene.

The 2-hydroxyarylaldoxime may be recovered from the reaction mixture in which it is prepared in any conventional manner for subsequent dehydration to the 2-hydroxybenzonitrile.

The dehydration step may be performed using conditions that have been fully described in the prior art for conversion of the —CH=NOH group to —CN. For examples of suitable dehydrating agents, reference is made to page 533 of Volume 2 of "Comprehensive Organic Chemistry" (Barton and Ollis) published by Pergamon Press and to pages 1038 and 1039 of the Fourth Edition of "Advanced Organic Chemistry" (Jerry March) published by John Wiley & Sons. Preferred dehydrating agents include acetic anhydride, thionyl chloride/dimethylformamide and sodium formate/formic acid. Dehydration may also be effected by azeotropic removal of water in the presence of an acid catalyst, for example p-toluenesulphonic acid, sulphuric acid or a solid supported acid such as an acid polymer or an acid clay. Whilst the 2-hydroxyarylaldoxime may be isolated from the oximation reaction mixture for dehydration, it is preferred to avoid isolation and to subject the crude oximation reaction mixture to dehydration after physical removal of water therefrom by, for example, simple separation or azeotropic distillation.

Alternatively, the method of the invention may be operated as a one-pot process whereby the aldehyde, at least partially in the salt and/or complex form, is converted directly to the nitrile via an aldoxime intermediate using, for example, conditions described in the prior art for such conversion.

The 2-hydroxybenzonitrile may be recovered from the reaction mixture in which it is prepared (and purified if necessary) using conventional methods.

Methods for the preparation of 2-hydroxyarylaldehydes by the ortho-formylation of optionally substituted phenols in the presence of various metal derivatives have been described in the aforementioned EP-A-0529870, EP-A-0077279, EP-A-0106653 and U.S. Pat. No. 4,231,967. In accordance with these methods, 2-hydroxyarylaldehydes are believed to be obtained at least partially in the form of metal salts and/or complexes from which the aldehyde itself may be recovered by conventional techniques, for example by acidification and extraction. It is a particularly advantageous feature of the present invention that the 2-hydroxyarylaldehyde metal salts or complexes obtained in said formylation processes may be used directly as starting materials without needing to isolate the hydroxyaldehydes themselves.

Accordingly, a further aspect of the present invention provides a method for the preparation of a 2-hydroxybenzonitrile which comprises reacting hydroxylamine with a 2-hydroxyarylaldehyde which is at least partially in the form of a salt and/or complex of a metal of Group II, Group III, Group IVA or Group VIA of the Periodic Table and is the direct product of reacting a phenol having at least one free ortho position with formaldehyde or a formaldehyde-liberating compound under substantially anhydrous conditions in the presence of a compound of a metal of Group II, Group III, Group IVA or Group VIA of the Periodic Table and/or under such conditions that the phenol is at least partially in the form of a salt and/or complex of a metal of Group II, Group III, Group IVA or Group VIA of the Periodic Table, and dehydrating the 2-hydroxyarylaldoxime so formed.

The expression "direct product" as used herein means a product that has not been isolated from the reaction mixture in which it is formed.

In a preferred embodiment of this aspect of the invention, hydroxylamine or a hydroxylamine salt is reacted with a magnesium 2-formylphenoxide obtained by reacting a magnesium bis-hydrocarbyloxide, derived at least in part from a hydroxyaromatic compound having at least one free position ortho to the hydroxyl group, with formaldehyde or a formaldehyde liberating compound under substantially anhydrous conditions.

In an especially preferred embodiment of this aspect of the invention, hydroxylamine or a hydroxylamine salt is reacted with a magnesium bis(2-formylphenoxide) obtained by reacting a magnesium bis-phenoxide derived from a phenol having at least one free ortho position with formaldehyde or a formaldehyde-liberating compound under substantially anhydrous conditions.

The substantially anhydrous conditions required by the formylation reaction for production of the magnesium bis (2-formylphenoxide) may be conveniently provided by the use of substantially anhydrous reactants together with conventional techniques, for example distillation, for removal of adventitious moisture. It is usually advantageous to perform the reaction in the presence of a substantially anhydrous solvent system. Suitable solvent systems typically comprise an inert non-polar or low polarity organic solvent and/or a polar organic solvent capable of acting as a ligand with respect to magnesium atoms.

Suitable inert non-polar or low polarity organic solvents will be liquids at the reaction temperature and will act as solvents for the magnesium bis-hydrocarbyloxide. Preferably, they will allow removal of one or more of the volatile by-products by distillation. Examples of suitable inert solvents include aromatic hydrocarbons, for example xylene, mesitylene, cumene, cymene, tetralin and, especially, toluene and chlorinated aromatic hydrocarbons, for example chlorobenzene and o-dichlorobenzene. Mixtures of inert solvents may be used.

Suitable polar solvents will be liquids at the reaction temperature and may be regarded as co-solvents when used in conjunction with non-polar or low polarity solvents. As examples of suitable polar co-solvents, there may be mentioned polar aprotic solvents such as dimethylsulphoxide, sulpholane, dimethylacetamide, N-formylpiperidine, N-methylpyrrolidinone, tetramethylurea and, especially, dimethylformamide, tertiary bases such as triethylamine, tri-octylamine, tetra-methylethylenediamine and pyridine, ethers such as diethyl ether, diphenyl ether, tetrahydrofuran, glyme, diglime, triglyme, tris[2-(2-methoxyethoxy)ethyl] amine and crown ethers and other polar solvents such as "Polymeg" 1000 and "Cellosolve" and the like. Particularly useful co-solvents include lower alkanols such as ethanol and, especially, methanol. Mixtures of co-solvents may be used. The co-solvent may be incorporated into the reaction mixture as such or in the form of a ligand already complexed with the magnesium atoms of the bis-hydrocarbyloxide.

Some solvent materials may have the ability to function as both "solvent" and "co-solvent" in the formylation reaction. Thus, for example, a material such as tetrahydrofuran may be used as a solvent in conjunction with a higher polarity co-solvent or as a co-solvent in conjunction with a lower polarity solvent or it may be used as the sole solvent/co-solvent.

The formylation reaction used to prepare the magnesium bis-(2-formylphenoxide) is suitably performed at a reflux temperature within the range from about 60° to about 130° C., by-products of the reaction, for example methanol, methyl formate and methylal, preferably being removed from the reaction mixture as they are formed. The reflux temperature, in any particular case, will depend upon the constitution of the solvent system and upon the pressure being exerted on the reaction zone. Formylation may be satisfactorily performed at atmospheric or higher pressures but, in some cases, it is preferred to carry out the formylation at reduced pressures, that is to say at pressures lower than normal atmospheric pressure, for example at pressures of from 50 to 700 mm Hg (absolute). In particular, it has been found that, in addition to facilitating removal of volatile reaction by-products, a significant improvement in the yield and/or purity of aldehyde and an appreciable reduction in formation of by-products can often be observed when the reaction is carried out at reduced pressure (and consequently at a lower temperature) compared with carrying out the same reaction in the same solvent system at atmospheric pressure.

In some cases, it may be preferable to carry out the reaction at a reflux temperature in the range from about 70° to about 80° C., for example about 75° C., the reaction pressure being selected to maintain distillation of reaction by-products. Pressures in the range from about 50 to about 500 mm Hg (absolute) will generally provide the preferred reflux temperatures.

Magnesium bis-hydrocarbyloxides which may be used in the formylation reaction are compounds containing two hydrocarbyloxy residues per magnesium atom, at least one of said hydrocarbyloxy residues being aryloxy, for example phenoxy or naphthyloxy, having at least one free position ortho to the oxygen atom. Especially suitable are magnesium bis-phenoxides wherein the phenoxide residues may be unsubstituted or may be substituted in any or all of the positions, other than both the 2- and 6-positions, by substituents which do not interfere with the course of the reaction and which preferably are electron-donating or weakly electron-withdrawing.

Especially useful magnesium bis-phenoxides are derivatives of phenols of the formula:

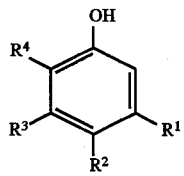

(2)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy, acyl or hydroxy group. Each of the various hydrocarbyl, hydrocarbyloxy and acyl groups which may be represented by $R^1$, $R^2$, $R^3$ and $R^4$ suitably contains up to 36 carbon atoms, for example from 1 to 6 carbon atoms.

The magnesium bis-phenoxides derived from phenols of Formula 2 may be regarded as compositions containing structures of Formula 3 as well as related but more complex structures containing more than one magnesium atom per molecule.

In structures of Formula 3:

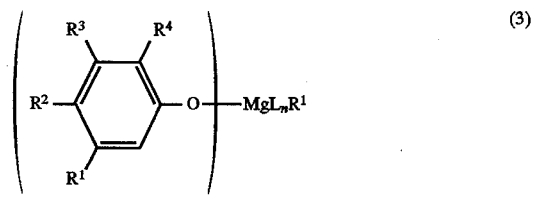

(3)

each of $R^1$, $R^2$, $R^3$ and $R^4$ is as defined above, L represents a ligand molecule derived from another component of the formylation reaction mixture and n represents an integer from 1 to 6.

Components of the formylation reaction mixture which may provide the ligand molecules L include the co-solvent, formaldehyde and the methanol by-product and mixtures thereof.

It is particularly convenient, however, to use a magnesium bis-hydrocarbyloxide which, because of its method of preparation, already contains appropriate ligand molecules.

Thus, it is preferred to use a magnesium bis-hydrocarbyloxide which has been prepared by the method described by Ramirez et al in Synthesis, 1979, 71, that is to say by reacting a magnesium alkoxide of the formula:

$$Mg(OR^5)_2 \qquad (4)$$

wherein $R^5$ represents an alkyl, for example a $C_{1-4}$-alkyl, radical, especially methyl, with up to two moles of a phenol having at least one unsubstituted position adjacent to the phenolic hydroxyl group, for example a phenol of Formula 2. Preferred ratios are from 0.9 to 2, especially from 1.5 to 2, typically about 1.66, moles of phenol per mole of magnesium alkoxide.

The magnesium bis-aryloxides, when used in the formylation reaction contain two aryloxy residues per magnesium atom and are believed also to contain one or more ligand molecules or groups, for example methanol molecules, such that they correspond or are structurally analogous to Formula 3. It is to be understood, however, that the present invention is not based upon any theory as to the precise structure of the magnesium bis-aryloxides and is to be regarded as relating to the use of said bis-aryloxides whether in the form of complexes of Formula 3 or not.

Other magnesium bis-hydrocarbyloxides which may be used in the method of the invention include compounds containing one aryloxy and one other hydrocarbyloxy, for example alkoxy, residue per magnesium atom. Such bis-hydrocarbyloxides may be obtained, for example, by reacting one mole of a magnesium alkoxide of Formula 4 with approximately one mole of a phenol having at least one unsubstituted position adjacent to the phenolic hydroxyl group and may, if desired, be used alone or in admixture with the aforementioned bis-aryloxides.

The formaldehyde used in the formylation reaction may be in the form of free gaseous formaldehyde or a solution in an anhydrous solvent or a formaldehyde-liberating compound, that is to say a compound capable of liberating formaldehyde under the conditions employed in the method of the invention. Suitable formaldehyde-liberating compounds include polymeric forms of formaldehyde such as paraformaldehyde. It is preferred to add the formaldehyde or formaldehyde-liberating compound gradually (continuously or discontinuously) to the bis-aryloxide in the solvent system.

The formaldehyde or formaldehyde-liberating compound is generally employed in the method of the invention in an amount of at least two moles, expressed as formaldehyde (HCHO), per mole of phenol present in the bis-hydrocarbyloxide. Preferred ratios are from 2 to 3, typically about 2.75 moles of formaldehyde per mole of phenol in the bis-hydrocarbyloxide. The co-solvent is suitably used in an amount not exceeding 5 moles per mole of bis-hydrocarbyloxide, preferred amounts being in the range from 1 to 2 moles per mole of bis-hydrocarbyloxide. These amounts include any co-solvent already present as ligand in the bis-hydrocarbyloxide. Since methanol is a by-product of the reaction, conversion and yield may be maximised by removing this methanol and any other volatile by-products by distillation during the course of the reaction so as to maintain the co-solvent/bis-hydrocarbyloxide ratio at the optimum level.

In a further valuable embodiment of the invention, hydroxylamine or a salt thereof may be reacted directly with the aluminium, titanium, zirconium or chromium derivatives of 2-hydroxyarylaldehydes obtained in the formylation reactions described in EP-A-0077279, EP-A-0106653 and U.S. Pat. No. 4,231,967 without the need to isolate the hydroxyaldehydes themselves from the reaction mixtures in which they are formed, the oxime so formed then being dehydrated.

The method of the invention is of particular value for the preparation of 2-hydroxybenzonitrile itself, especially by an integrated process comprising the steps of 1) reacting magnesium bis-phenoxide with formaldehyde or a formaldehyde-liberating compound under substantially anhydrous conditions to form the magnesium salt of salicylaldehyde, said magnesium bis-phenoxide having been obtained by reacting phenol with a magnesium alkoxide of formula 4;

2) reacting the magnesium salt of salicylaldehyde with hydroxylamine or a salt thereof whereby to form salicylaldoxime; and 3) dehydrating the salicylaldoxime.

Preferably, the integrated process is operated without isolation of either the salicylaldehyde magnesium salt or the salicylaldoxime.

The invention is illustrated but not limited by the following Examples.

EXAMPLE 1

Methanol (256 ml), toluene (112 ml), magnesium metal (0.6 g) and magnesium methoxide (10 ml of 8% solution in methanol) were charged to a 2l reaction vessel and heated to 62°–64° C. and maintained at this temperature for 2 hours under nitrogen.

Meanwhile, a solution of phenol (94 g) in toluene (100 ml) was prepared and added to the reaction mixture, which was then stirred for a further 1 hour at 64° C. The apparatus was then set for distillation and the contents of the reaction flask were heated to 90° C. to enable distillation of methanol at 67° C. Extra toluene (300 ml) needed to be added gradually to prevent the mixture becoming a solid. When most of the methanol (approx 300 ml) had been distilled off, paraformaldehyde (90 g) in a toluene slurry (140 ml) was added over 1 hour at 90° C. and then washed in with toluene (100 ml). The methanol produced was distilled off during addition. The reaction was then left to distil for a further 1 hour to ensure all the methanol had been removed. A solution of hydroxylamine sulphate (172.2 g) in toluene (100 ml) was then added over 1 hour at 45° C. and stirred for 3 hours at 45° C. G.C. analysis indicated that the reaction was complete with 88.9% oxime and 2% phenol present.

The reaction mixture was then washed with a solution of one mole equivalent sulphuric acid (98 g) in water (300 ml), followed by water (4×150 ml) to afford an acid-free solution. The toluene was then removed at 50° C./20 mm Hg to afford a yellow solid.

Wt of oxime=126.2 g

GC strength vs standard=88.9%

Percentage yield of salicylaldoxime based on initial phenol charged=81.9%

Percentage yield of salicylaldoxime based on reacted phenol=85.3%

Oxime (13.7 g) and formic acid (150 ml) were stirred at ambient temperature under nitrogen for 10 minutes, sodium formate (13.8 g) was then added over 2 minutes and the reaction mixture was gradually heated to reflux (110° C.) and maintained at this temperature for 4 hours. G.C. analysis indicated that the reaction was complete with 87% 2-cyanophenol and 2.7% oxime present.

The apparatus was then set for distillation and the formic acid was distilled off at 43° C./20 mm Hg. The reaction mixture was not allowed to solidify. After approximately 80 ml of formic acid had been removed, the reaction mixture was cooled to room temperature, then water (150 ml) was added followed by dichloromethane (150 ml) and stirred for a further 1 hour. The hererogenous solution was then washed with water (2×100 ml) and the combined aqueous phases were washed with dichloromethane (2×100 ml). The dichloromethane phases were combined and dichloromethane was removed at 40° C./20 mm Hg to afford an oil.

Wt of oil=9.42 g

GC vs standard=94.2%

Percentage yield of 2-cyanophenol based on oxime=82.8%

Percentage yield of 2-cyanophenol based on phenol consumed=86.4%

EXAMPLE 2

Methanol (128 ml), toluene (56 ml), magnesium (7.3 g) and magnesium methylate (10 ml of 8% solution in methanol) were charged to a dry, nitrogen purged flask and heated to reflux. The mixture was held at reflux until evolution of hydrogen had ceased and all the magnesium reacted to give a white suspension of magnesium methylate. Phenol (47 g), dissolved in toluene (200 ml), was charged to a dropping funnel and added rapidly to the stirred reaction slurry over 2 minutes causing the solid to dissolve to give a pale yellow solution.

The reaction flask was then modified for distillation and the flask contents were gradually heated and distilled up to an internal temperature of 95° C. During this period, the magnesium phenylate precipitated out of solution as the methanol was removed.

A preformed slurry of paraformaldehyde (45 g) in toluene (100 mi) was then added slowly over a period of 52 minutes whilst maintaining distillation at 95°–100° C. to remove the lower boiling components (methanol and methyl formate). The colour of the slurry rapidly turned from white to yellow during this addition. On completion of the addition, the slurry was stirred for a further hour.

The reaction mass was cooled to ambient temperature and concentrated sulphuric acid (15.34 g) added dropwise from a dropping funnel causing red droplets and striations to form. Further stirring at ambient temperature for 2 hours resulted in some solubilisation of the yellow solid. The flask was then modified for azeotropic distillation and hydroxylamine sulphate (98.4 g) and methane sulphonic acid (24.0 g) were added. The resulting mixture was heated to reflux. Water (7.1 ml), generated by the reaction was distilled off over a period of about 10 hours. The colour of the two phase reaction mass gradually darkened to a deep red brown colour during this period.

Water (200 ml) was added to the reaction mass and after stirring for 2 hours at ambient temperature the mixture was screened to remove a black oil phase. The toluene solution was separated from the filtrates and vacuum stripped to obtain the product. Further amounts of product were obtained from the immiscible oil/tar phase. The various fractions were analysed by quantitative GC vs internal standard and found to give a total isolated yield of 50.0% based on phenol charged.

EXAMPLE 3

Methanol (128 ml), toluene (56 ml), magnesium (7.3 g) and magnesium methylate (10 ml of 8% solution in methanol) were charged to a dry, nitrogen purged flask and heated to reflux. The mixture was held at reflux until evolution of hydrogen had ceased and all the magnesium reacted to give a white suspension of magnesium methylate. Phenol (47 g), dissolved in toluene (200 ml), was charged to a dropping funnel and added rapidly to the stirred reaction slurry over 2 minutes causing the solid to dissolve to give a pale yellow solution.

The reaction flask was then modified for distillation and the flask contents were gradually heated and distilled up to an internal temperature of 95° C. During this period, magnesium phenylate precipitated out of solution as the methanol was removed.

A preformed slurry of paraformaldehyde (45 g) in toluene (100 ml) was then added slowly over a period of 1 hour whilst maintaining distillation at 95°–100° C. to remove the lower boiling components (methanol and methyl formate). The colour of the slurry rapidly turned from white to yellow during this addition. On completion of the addition, the slurry was stirred for a further hour to ensure complete reaction (as judged by G.C. analysis).

The reaction mass was cooled to 45° C. and a solution of hydroxylamine sulphate (98.4 g) and sulphuric acid (15.34 g) in water (300 ml) was added from a dropping funnel over a period of 10 minutes maintaining the temperature at 45°–50° C. The two phase mixture was then stirred rapidly for 2 hours until the oximation was complete (as judged by G.C. analysis). The mixture was then transferred to a separating funnel and the lower aqueous layer separated off. The organic phase was washed with 5% sulphuric acid (100 ml) and then returned to the reaction flask.

The flask was modified for azeotropic distillation and the toluene solution heated to reflux and any water present azeotropically removed. The solution was then cooled to 95° C. and p-toluene sulphonic acid (4.36 g) added. The reaction solution was reheated to reflux for 2 to 3 hours until reaction was complete (as judged by G.C. analysis) and water generated by the dehydration reaction, was azeotropicalllly removed.

The reaction mixture was cooled to ambient temperature. Water (200 ml) was added and, after stirring for 2 hours at ambient temperature, the mixture was screened to remove any interface and the toluene phase was separated from the filtrates then vacuum stripped to obtain the product.

Weight of crude material=23.1 g

Strength (GC vs Int. Std)=40.3%

Yield (based on phenol)=31.3%

EXAMPLE 4

Into a 1.0 L round bottomed flask, fitted with a mechanical stirrer, thermometer, and reflux condenser, were charged dry methanol (150.0 ml), dry toluene (50.0 ml) and an 8% solution of magnesium methoxide in methanol (5.0 ml). To this was added magnesium raspings (5.85 g) and the reaction mixture was then heated to reflux. After several minutes, hydrogen evolution was noted. The mixture was then maintained at reflux for 60 minutes until all of the magnesium had dissolved, giving a cloudy white solution/suspension, with no further hydrogen evolution. Phenol (37.6 g) was added and the resulting slurry heated under reflux for 1 hour. Toluene (240.0 ml) was charged and the equipment rearranged for distillation with fractionation. The mixture was heated to remove the methanol as an azeotrope with toluene until an internal temperature of 95° C. was reached. During the distillation (at approx. 88° C.) the slurry became very viscous and a further addition of toluene was necessary (50.0 ml). A slurry of paraformaldehyde (36.0 g) in toluene (80 ml) was added in portions over 1 hour at 95° C. with concurrent distillation of solvent and low boiling by-products (62.0 ml). The reaction was held at 95° C. for 1½ hours before being cooled to room temperature over night under nitrogen. The equipment was then converted to reflux for the oximation reaction and heated to 55° C. A solution of hydroxylammonium sulphate (39.4 g) in water (120.0 g) was prepared at 40°–50° C. and added to the experiment over 30 minutes with rapid agitation. The reaction was continued for 2 hours at 55° C., then cooled to 30°–40° C. and the agitator stopped.

The contents of the reaction vessel were then transferred to a separation funnel. The aqueous layer was removed and the purple/black organic layer was transferred back to the reaction vessel. A cold dilute solution of sulphuric acid (13.8 g) in water (180.0 g) was charged to the vessel and agitated for 5–10 minutes at 10° C. A rapid colour change to yellow occurred in the first minute. After this acid treatment, the contents of the flask were again transferred to the separation funnel and the acidic aqueous layer was removed. The organic layer was then washed with water (2×100 ml) until acid free. The aqueous layers were combined and pH adjusted to 2–3 before being extracted with dichloromethane (2×100 ml). The original toluene layer and the dichloromethane extracts were then combined and the solvents were removed by rotary evaporation to yield 57.5 g of a beige solid which was found to be 86.6% strength by G.C. analysis using a sample of salicylaldoxime of known strength as a standard. This gives a yield of 90.9%. The main impurity in the product was shown to be 2-cyanophenol at 3.2% strength, giving a further useful yield of 3.85%, (i.e. a total useful yield of 94.75%).

The salicylaldoxime from the above was then dehydrated in the following way to give the desired 2-cyanophenol.

Into a dry 500 ml multi-necked flak (equipped with a gas-tight stirrer, thermometer, pressure equalising dropping funnel and a dichloromethane/Drikold cooled reflux condenser, with caustic-soda scrubber) were charged the crude salicylaldoxime from the previous stage (15.82 g; containing: salicylaldoxime, 86.6% strength and 2-cyanophenol, 0.51 g) and toluene (100 ml) to afford a solution which was heated to 93°–95° C. and maintained at this temperature for 30 minutes. A phosgene/toluene solution (74.1 g of 20% soln.) was then added dropwise, via dropping funnel, over 45 minutes maintaining the temperature at 93°–95° C. During the addition, a pale yellow/green suspension was formed which was solubilised towards the end of the addition to give a yellow solution. The reaction mixture was left to stir at 93°–95° C. for a further 1 hour. G.C. analysis indicated no salicylaldoxime present therefore the reaction mixture was cooled to 70° C. at which time water (50 ml) was added dropwise over 30 minutes, whilst maintaining the temperature at 70°–72° C. After addition of water, the heterogeneous system was left to stir for a further 30 minutes to destroy any unreacted phosgene. Testing at this stage indicated no phosgene present. On cooling to room temperature there was evidence of a solid precipitating from the heterogeneous system. This solid (1.45 g) was filtered off prior to isolation of the product.

The aqueous and toluene phases were separated and the aqueous phase was extracted with dichloromethane (4×50 ml). The toluene layer and the dichloromethane extracts were then combined and the solvents were removed by rotary evaporation to give 11.9 g of a solid which was quantitatively analysed by G.C. to give a strength of 91.2%, and an overall yield of 82.9% from phenol starting material.

EXAMPLE 5

Into a dry 500 ml multi necked flask equipped with gas-tight stirrer, thermometer, condenser and nitrogen blanket were charged salicylaldoxime prepared as described in Example 4 (15.82 g) and acetic acid (150 ml). The mixture was stirred at ambient temperature under nitrogen for 10 minutes to afford a clear solution. Sodium acetate (8.35 g) was added over 2 minutes (on addition there was a slight exotherm of 4° C.) to afford a suspension which was then slowly heated to reflux (118°–119°) and maintained at this temperature for 10 hours. G.C. analysis at this point indicated that there was a 95% conversion of salicylaldoxime to products. The reaction mixture was then cooled to room temperature and the apparatus was then set up for vacuum distillation. After the bulk of the acetic acid (80 ml) was removed, water (150 ml) and dichloromethane (150 ml) were added and the heterogeneous mixture was stirred for 1 hour at ambient temperature under nitrogen.

The aqueous and dichloromethane phases were separated using a separating funnel and the aqueous phase was extracted with dichloromethane (4×25 ml). The solvents were then topped to afford 18 g of solid which was analysed quantitatively via G.C. to afford a strength of 67% and thus an overall yield of 93% based on phenol used in Example 4.

EXAMPLE 6

Into a dry 250 ml multi necked flask equipped with gas-tight stirrer, thermometer, condenser, Dean & Stark side arm and nitrogen blanket were charged salicylaldoxime prepared as described in Example 4 (15.82 g) and toluene (100 ml). The solution was heated to reflux (110°–111° C.) and left to stir for a further 1 hour to azeotrope off any water present in the solution. Meanwhile the dehydrating reagent was prepared by charging toluene (34 ml), dimethylformamide (11 ml) and thionyl chloride (7 ml) to a dropping funnel. After 5 minutes, a heterogeneous solution was formed and the bottom layer containing the SOCl$_2$-DMF dehydrating reagent was removed and charged to a further dropping funnel, when it was then added dropwise to the reaction mixture at reflux to afford a yellow suspension. After 2 hours at reflux, it was evident that there was still 5% salicylaldoxime present therefore a further batch of the dehydrating reagent (made up as previously stated) was added to the reaction mixture and stirred at reflux for a further 1 hour. G.C. analysis indicated 100% conversion of salicylaldoxime to products with 71% (Area %) 2-cyanophenol.

EXAMPLE 7

Into a dry 250 ml multi necked flask equipped with gas-tight stirrer, thermometer, condenser, Dean & Stark side arm and nitrogen blanket were charged salicylaldoxime prepared as described in Example 4 (15.82 g) and toluene (100 ml). The solution was heated to reflux (110°–111° C.) and left to stir for a further 1 hour to azeotrope off any water present in the solution. Para-toluene sulphonic acid (19.00 g) was then charged and stirred for a further 4 hours at reflux, after which G.C. analysis indicated that the reaction had reached equilibrium with 79% conversion of salicylaldoxime to products. The reaction was then cooled to room temperature. Water (50 ml) was then added to the reaction mixture, the pH was taken to 1 using concentrated sulphuric acid and stirred at ambient temperature for 15 minutes.

The aqueous and toluene phases were separated using a separating funnel and the aqueous phase was extracted with fresh toluene (4×25 ml). The solvents were then topped to afford 31 g of solid, which was analysed quantitatively via G.C. to afford a strength of 27% and thus an overall yeild of 64% based on phenol (refer to Example 4).

EXAMPLE 8

Into a dry 250 ml multi necked flask equipped with gas-tight stirrer, thermometer, condenser, Dean & Stark side arm and nitrogen blanket were charged salicylaldoxime prepared as described in Example 4 (15.82 g) and toluene (100 ml). The solution was heated to reflux (110°–111° C.) and left to stir for a further 1 hour to azeotrope off any water present in the solution. Concentrated sulphuric acid (5 g) was then added to the reaction dropwise and the reaction was left to stir at reflux for 2 hours. G.C. analysis indicated 100% conversion of salicylaldoxime to products. The reaction mixture was then cooled to room temperature. Water (50 ml) was added to the reaction mixture which was then stirred at ambient temperature for 1 hour.

The reaction mixture was transferred to a separating funnel and the aqueous and toluene phases were separated. The aqueous phase was extracted using dichloromethane (4×25 ml). The solvents were then topped to afford 13 g of solid, which was analysed quantitatively via G.C. to afford a strength of 89% and thus an overall yield of 88% based on phenol (refer to Example 4).

EXAMPLE 9

Into a dry 250 ml multi-necked flask equipped with gas tight stirrer, thermometer, pressure equalising dropping funnel and a dichloromethane/Drikold cooled reflux condenser (connected to an aqueous caustic scrubber) were charged salicylaldoxime prepared as described in Example 4 (15.82 g) and toluene (100 ml) to afford a solution which was heated to 93°–95° C. and stirred at this temperature for 0.5 hour. A solution of phosgene in toluene (89.1 g of 20% ww soln.) was then added dropwise, via a dropping funnel, over 0.75 hour whilst maintaining the temperature at 93°–95° C. to afford a pale yellow suspension. The temperature was maintained for 2 hours, after which G.C. analysis indicated reaction was complete. The apparatus was carefully set for atmospheric distillation (ensuring that the equipment was still connected to the caustic scrubber) and the toluene was distilled off up to an internal temperature of 120° C. to give 2-cyanophenol in 92.5% yield based on the phenol used in Example 4.

I claim:

1. A method for the preparation of 2-hydroxybenzonitrile which comprises reacting hydroxylamine or hydroxylamine salt with a 2-hydroxyarylaldehyde which is at least partially in the form of a salt and/or complex of a metal of Group II, Group III, Group IVA or Group VIA of the Periodic Table and dehydrating the 2-hydroxyarylaldoxime so formed.

2. A method according to claim 1 wherein the metal is magnesium, aluminium, titanium, zirconium or chromium.

3. A method according to claim 1 or claim 2 wherein reaction between hydroxylamine or hydroxylamine salt and the aldehyde and dehydration of the aldoxime are effected in a single reaction step.

4. A method according to any one of claims 1 to 3 wherein the 2-hydroxyarylaldehyde is the direct product of reacting a phenol having at least one free ortho position with formaldehyde or a formaldehyde-liberating compound under substantially anhydrous conditions in the presence of a compound of a metal of Group II, Group III, Group IVA or Group VIA of the Periodic Table and/or under such conditions that the phenol is at least partially in the form of a salt and/or complex of a metal of Group II, Group III, Group IVA or Group VIA of the Periodic Table.

5. A method according to claim 4 which comprises reacting the hydroxylamine or a hydroxylamine salt with a magnesium 2-formylphenoxide obtained by reacting a magnesium bis-hydrocarbyloxide derived at least in part from a hydroxyaromatic compound having at least one free position ortho to the hydroxyl group with formaldehyde or a formaldehyde liberating compound under substantially anhydrous conditions.

6. A method according to claim 5 wherein the magnesium 2-formylphenoxide is a magnesium bis(2-formylphenoxide) obtained by reacting a magnesium bis-phenoxide derived from a phenol having at least one free ortho position with formaldehyde or a formaldehyde-liberating compound under substantially anhydrous conditions.

7. A method according to claim 5 or claim 6 wherein the magnesium 2-formylphenoxide is the product of reacting the magnesium bis-hydrocarbyloxide with formaldehyde or a formaldehyde-liberating compound in the presence of a substantially anhydrous solvent system comprising an inert non-polar or low polarity organic solvent and a polar organic solvent.

8. A method according to claim 7 wherein the inert organic solvent comprises an aromatic hydrocarbon or a chlorinated aromatic hydrocarbon.

9. A method according to claim 8 wherein the aromatic hydrocarbon comprises toluene or xylene.

10. A method according to claim 7 wherein the polar organic solvent comprises a polar aprotic solvent or a lower alkanol.

11. A method according to claim 10 wherein the lower alkanol comprises methanol.

12. A method according to claim 5 wherein the magnesium bis-hydrocarbyloxide is a magnesium bis-phenoxide derived from a phenol of the formula:

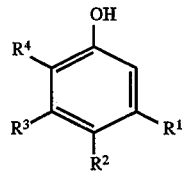 (2)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy, acyl or hydroxy group.

13. A method according to claim 12 wherein each of the alkyl, cycloalkyl, aralkyl, aryl, alkaryl, alkoxy, aryloxy or acyl groups which may be represented by $R^1$, $R^2$, $R^3$ and $R^4$ contains from 1 to 36 carbon atoms.

14. A method according to claim 5 wherein the magnesium bis-hydrocarbyloxide is the product of reacting a magnesium alkoxide of the formula $$Mg(OR^5)_2 \qquad (4)$$

wherein $R^5$ represents an alkyl radical with up to two moles of a phenol having at least one unsubstituted position ortho to the hydroxyl group.

15. A method according to claim 14 wherein the magnesium bis-hydrocarbyloxide is the product of reacting the magnesium alkoxide with from 0.9 to 2 moles of phenol per mole of magnesium alkoxide.

16. A method according to claim 14 or claim 15 wherein the magnesium alkoxide is magnesium methoxide.

17. A method according to claim 1 wherein the 2-hydroxyarylaldehyde is salicylaldehyde.

18. A method according to claim 17 which comprises the steps of:

1. reacting magnesium bis-phenoxide with formaldehyde or a formaldehyde-liberating compound under substantially anhydrous conditions to form the magnesium salt of salicylaldehyde, said magnesium bis-phenoxide having been obtained by reacting phenol with a magnesium alkoxide of formula 4;

2. reacting the magnesium salt of salicylaldehyde with hydroxylamine or a salt thereof whereby to form salicylaldoxime; and 3. dehydrating the salicylaldoxime.

* * * * *